(12) United States Patent
Brandenberg

(10) Patent No.: US 6,239,876 B1
(45) Date of Patent: May 29, 2001

(54) OPTICAL DETECTOR DEVICE

(75) Inventor: Albrecht Brandenberg, March (DE)

(73) Assignee: Fräunhofer-Gesellschaft zur Förderung der Angewandten Forschung e.V., Munich (DE)

( * ) Notice: Subject to any disclaimer, the term of this patent is extended or adjusted under 35 U.S.C. 154(b) by 0 days.

(21) Appl. No.: 09/495,160

(22) Filed: Jan. 31, 2000

Related U.S. Application Data

(63) Continuation of application No. PCT/EP98/03281, filed on Jun. 2, 1998.

(30) Foreign Application Priority Data

Jul. 29, 1997 (DE) .............................................. 197 32 619

(51) Int. Cl.⁷ ....................................................... G01J 3/45
(52) U.S. Cl. ............................................. 356/451; 385/12
(58) Field of Search ................................... 356/346, 361; 385/12, 129

(56) References Cited

U.S. PATENT DOCUMENTS

| | | |
|---|---|---|
| 4,229,105 | 10/1980 | Silverbåge . |
| 5,120,131 * | 6/1992 | Lukosz ................................ 356/351 |
| 5,168,325 | 12/1992 | Yoder-Short . |
| 5,173,747 * | 12/1992 | Boiarski et al. ..................... 356/361 |
| 5,239,364 | 8/1993 | Matsuzaki . |
| 5,325,172 * | 6/1994 | Kataoka et al. ..................... 356/349 |
| 5,426,505 | 6/1995 | Geiser et al. . |

FOREIGN PATENT DOCUMENTS

| | | |
|---|---|---|
| 197 32 619 C2 | 8/1999 | (DE) . |
| 0283047 | 9/1988 | (EP) . |
| 0340577 | 11/1989 | (EP) . |
| 0481440 | 4/1992 | (EP) . |
| 2228082 | 8/1990 | (GB) . |
| WO9712225 | 4/1997 | (WO) . |

OTHER PUBLICATIONS

Bo Liedberg et al., "Surface Plasmon Resonance For Gas Detection And Biosensing", Elsevier Sequoia/Printed in The Netherlands, Sensors and Actuators, 4 , pp. 299–304, (1983).

Ph. M. Nellen et al. "Integrated Optical Input Grating Couplers As Biochemical Sensors" Elsevier Sequoia/Printed in The Netherlands, Sensors and Actuators, 15, pp. 285–295, (1988).

R. Cush et al. "The resonant mirror: a novel optical biosensor for direct sensing of biomolecular interactions Part I: Principle of operation and associated instrumentation", Elsevier Science Publishers Ltd., Biosensors & Bioelectronics 8, pp. 347–353, (1993).

P.E. Buckle et al. "The resonant mirror: a novel optical sensor for direct sensing of biomolecular interactions Part II: Applications", Elsevier Science Publishers Ltd., Biosensors & Bioelectronics 8, pp. 355–363, (1993).

(List continued on next page.)

*Primary Examiner*—Frank G. Font
*Assistant Examiner*—Philip Natividad
(74) *Attorney, Agent, or Firm*—Akin, Gump, Strauss, Hauer & Feld, L.L.P.

(57) ABSTRACT

The present invention relates to an optical detector device, in particular for analyzing substances, mixtures of substances or chemical reactions and for determining refractive indices, the device comprising a light source, a measurement path and a reference path and an optoelectronic detection means, with an optical divider being provided downstream of the light source for forming two radiation sources for divergently radiated light beams, of which one is assigned to the measurement path and one to the reference path, and the phase velocity of the light being influenced at least in the measurement path, and the divergent light beams being superimposed in the area of the optoelectronic detection means to form a characteristic intensity distribution.

32 Claims, 4 Drawing Sheets

OTHER PUBLICATIONS

A. Brandenburg et al., "Integrated optical Young interferometer" *Applied Optics,* vol. 33, No. 25, pp. 5941–5947, (1994).

J. Chen et al., "Quantitative Measurement of a Phase Object by Fringe Scanning Interference Microscopy", Applied Optics vol. 28, No. 9, pp. 1615–1617 (May 1, 1989).

* cited by examiner

OPTICAL DETECTOR DEVICE

This is a continuation of PCT application No. PCT/EP 98/03281, filed Jun. 2, 1998.

The present invention relates to an optical detector device according to the preamble of claim 1 for determining or influencing the phase velocity of light guided in a waveguide or propagating freely in space.

For the detection of chemical reactions or for the analysis of substances or mixtures of substances and for the determination of the refractive index of a medium or the difference in the refractive indices of two liquids or gases, a high-quality detector system which is not prone to failure and composed of a few components in a relatively simple manner is needed by the users.

Interferometric or differential-refractory measuring cells and measuring means are known for such a purpose from the prior art (U.S. Pat. No. 4,229,105, U.S. Pat. No. 5,168,325, U.S. Pat. No. 5,426,505).

A direct detection of chemical or biochemical reactions, i.e. a detection without the use of labels (e.g. by fluorescence or radioactivity) can inter alia be carried out by sensing the propagation velocity of a light wave in dependence upon its being influenced or affected by the substance (detection medium) to be detected. The influencing medium (detection medium) is then inferred from the change in propagation velocity. The change in the propagation velocity of light waves can be detected by means of various optical assemblies. Frequently, the velocity measurement is based on an angular measurement. In such a case both the light rays freely propagating in space and light guided in the waveguides are used. As is known, the guidance of light in an optical waveguide is accompanied by an evanescent field part which is guided outside the optical waveguide. Therefore, it is possible with optical waveguides to detect mass deposits on the surface of the optical waveguide (strictly speaking, on the surface of the light-conducting layer of the optical waveguide).

In the instant field, the interest has specifically been directed to two measuring principles, namely surface plasmon resonance (B. Liedberg, C. Nylander, I. Lundström: Surface plasmon resonance for gas detection and biosensing; Sensors and Actuators 4 (1983), 299) and the principle of the grating coupler (Ph. Nellen, K. Tiefenthaler, W. Lukosz: Integrated optical input grating couplers as biochemical sensors; Sensors and Actuators 15 (1988) 285). In both cases the propagation constant of a guided light wave is determined on the basis of an angular measurement. In this process the fact is exploited that the excitation of the surface plasmon and of the waveguide mode, respectively (in the case of the grating coupler), during radiation onto the thin-film element is only possible within a very small angular range. This angular range is shifted in dependence upon the absorption of molecules on the surface of the structural element or component. The sensitivity of the two measuring methods as to a surface deposition with antibodies and antigens, respectively, is about the same. However, it is limited by the fact that the center of the angular range in which coupling is possible can be determined at an accuracy of about $1 \times 10^{-3}$ of said angular range.

Another method, the so-called "resonant mirror" principle, also ascribes the change in propagation velocity to an angular measurement (R. Cush, J. Cronin, W. Steward; C. Maule, J. Molloy; N. Goddard: The resonant mirror: a novel optical biosensor for direct sensing of biomolecular interactions, Part I: Principle of operation and associated instrumentation, Biosensors & Bioelectronics 8 (1993) 347).

Recently, integrated optical components have increasingly been used for interferometric purposes, e.g. the Mach-Zehnder interferometer or the Young interferometer (e.g. as a layer waveguide for detecting magnetic field strengths, voltages or temperatures, for refractrometry or chemical substance detections). Said integrated optical systems are very compact and mechanically stable. In the technical field of such planar optical waveguides special attention must be paid to the problems regarding fiber and light coupling into said integrated optical systems, and also to the achievement of definite measurement results because of the periodic structure of interferometrically obtained intensity distributions.

The improvement of said existing systems in the sense of a high-resolution optical detector device which for reasons of costs and for decreasing the proneness to failure should be composed of a few optical components and in a simple manner is desired by the users. Moreover, the device should permit the design as a multichannel system so that many analyses (preferably more than 100 analyses) can be carried out in parallel in one operation. Analytical assemblies which evaluate chemical or biochemical reactions on the surface of an optical waveguide require inexpensive and easily replaceable waveguide components because the immobilization of specific substances for detecting the analyte (detection medium) can only be maintained to a limited degree. In particular, only a limited number of analyses can normally be carried out with one immobilization.

It is therefore the object of the present invention to provide an optical detector device which meets the aforementioned requirements and permits a desired, substance-specific detection in an uncomplicated and inexpensive manner.

Said object is achieved according to the invention by the features of claim 1.

The beam formation intended according to the invention and regarding the light received from a light source to obtain two radiation sources radiating divergent light permits—upon actuation of the one beam with a reference medium (reference path) and upon actuation of the other beam with a detection medium (measurement path)—a simple superimposition of the divergent beams in the detection plane in which a local resolution detector (preferably a CCD line) is positioned for detecting the characteristic intensity distribution.

The resulting line pattern corresponds to the signature as is known from the double slit experiment. Said signature (intensity distribution) changes whenever the phase velocity of the light is changing in one of the action paths (measurement path or reference path). The analysis of the diffraction pattern which is carried out by the local resolution detector permits the quantitative determination of the phase difference at the end of measurement path and reference path (action paths) and thus the analysis of a specific substance, of mixtures of substances or chemical reactions, and also the determination of the refractive indices of two liquids or gases by irradiation of the media, which are preferably positioned in a double cell or cuvette, by the beams.

In a particularly preferred embodiment, an analysis by way of fluorescence measurement can additionally be made by exploiting the fluorescence of the detection medium (or the reference medium).

Preferred embodiments of the subject matter of the invention are shown in the subclaims.

The invention shall now be explained in more detail with reference to embodiments and associated drawings, in which.

Figure 1:
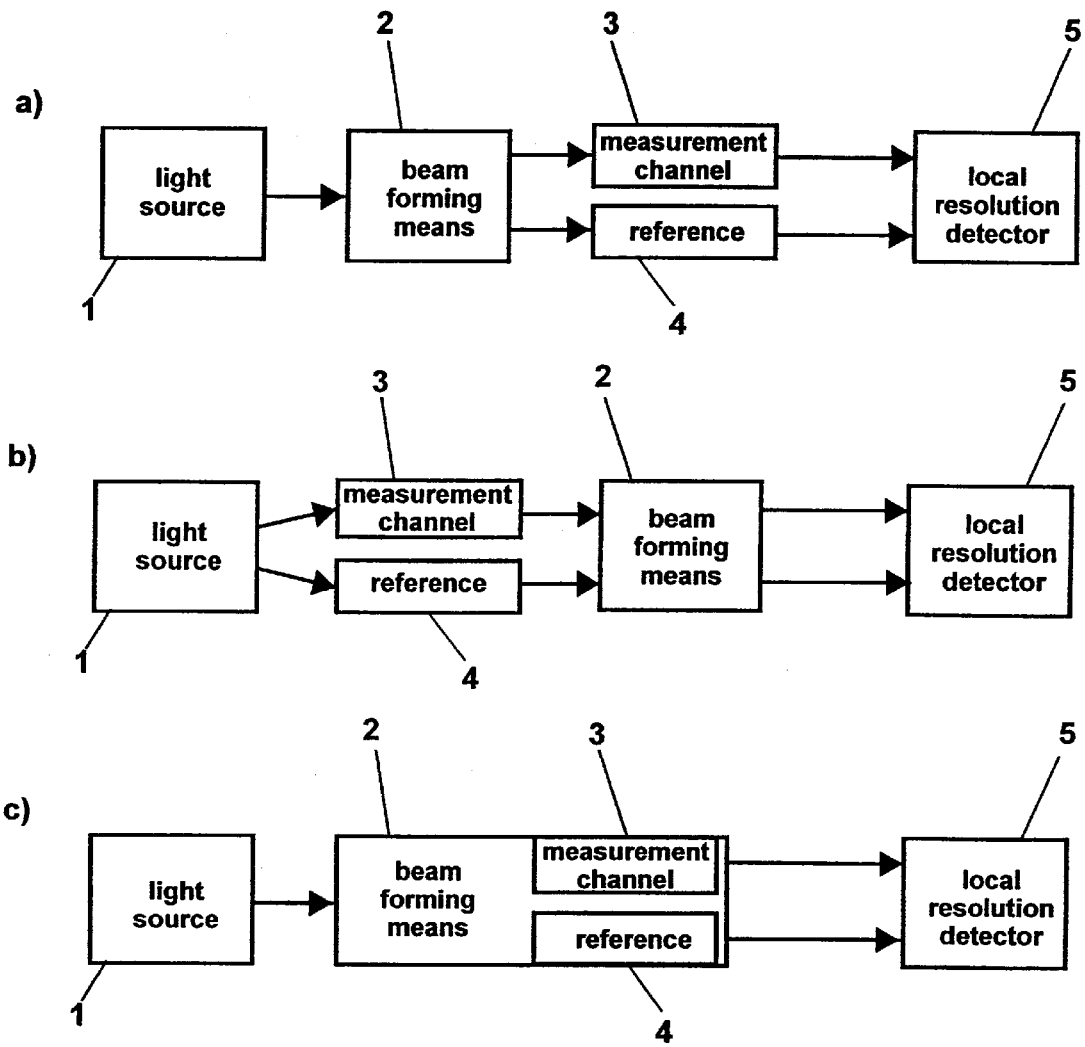
FIGS. 1a–1c are schematic illustrations showing the structural design of optical detector devices according to various embodiments of the present invention.

First of all reference is made to FIGS. 1a to 1c which are block diagrams showing various possibilities of designing the optical detector device.

In all cases the detector device consists of a (single) light source 1, an optical arrangement (optical beam-forming means 2) for producing two divergently radiating, spatially restricted intensity distributions (radiation sources) which are as point-shaped as possible, an action region consisting of a measurement path 3 and a reference path 4, in which light is guided along or through the substances to be analyzed, and of a photoelectric receiving means 5 (local resolution detector).

Such an optical detector device is schematically shown in FIGS. 1a to 1c. The action path consisting of measurement path 3 and reference path 4 may be arranged in front of or behind the optical splitter or divider 2 (optical beam-forming means). These two embodiments are shown in FIGS. 1a and 1b.

As shown in FIG. 1c, the optical divider (optical beam-forming means 2) can also be made integral with the measurement path 3 (measurement channel) and the reference path 4 (reference channel), i.e. with the action region in an integrated optical element (IO element), preferably a planar optical waveguide (layer waveguide), as will be explained in more detail with reference to further embodiments.

The two divergent beams are superimposed along the path following the optical beam-forming means 2. In a detection plane which accommodates the local-resolution optoelectronic receiving means, preferably a CCD line 5, which allows a positional interpretation of the intensity distribution, the beams produce an intensity distribution which is characteristic of the sample analyzed. The resulting line pattern corresponds to the signature created in the known double slit experiment. Said pattern will change when the phase velocity of the light changes in one of the action paths, i.e. either in the measurement path 3 or in the reference path 4. The analysis of the diffraction pattern allows the quantitative determination of the phase difference at the end of measurement path 3 and reference path 4.

Figure 2:
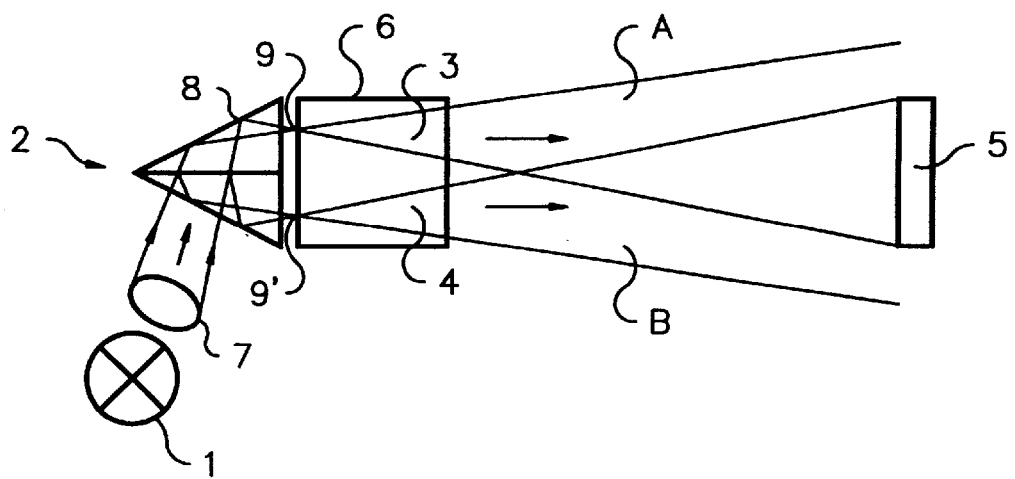
FIG. 2 is a schematic view showing an optical detector device according to a further embodiment of the invention with a beam forming means arranged upstream of the measurement path and the reference path, respectively (action channels or action paths)

An embodiment according to FIG. 1a is illustrated in FIG. 2. In FIG. 2 the optical beam-forming means 2 is arranged in the optical path between light source 1 and a planar optical waveguide 6 in which (here not shown in greater detail) the measurement path 3 and the reference path 4 are formed. The optical beam-forming means 2 consists of a focusing lens 7 and a Köster's prism 8. In the focal plane of the focusing lens 7, two bright light spots are created that divergently radiate into the space positioned therebehind. Whenever a planar optical waveguide 6 is arranged therein which without any lateral structurization of its light-conducting layer, which is preferably arranged on the surface, keeps the incident light in one plane, the beams will continue to diverge in the plane of the light-conducting coating while the light in a plane perpendicular to the light-conducting layer is concentrated onto the light-conducting layer. Of decisive importance to the generation of the diffraction pattern on the photoelectric detector 5 is the divergent propagation of the first and second light beams in the layer plane of the planar optical waveguide 6.

In the embodiment shown in FIG. 2, light is coupled from the Köster's prism 8 into the planar optical waveguide 6 and the light-conducting layer, respectively, through an end face of the planar optical waveguide 6. Radiation sources 9, 9' are created in said end face as output sources of the two light beams of the light guided in the light-conducting layer of the planar optical waveguide and form the measurement path 3 and the reference path 4. In the respective regions on the surface of the planar optical waveguide 6 (which surface is covered with the light-conducting layer), flow cells (here not shown) are e.g. placed by which the analytes (detection media) are supplied in the region of the measurement path 3, and reference liquids via the reference path 4, and exposed to the evanescent field of the light guided in the light-conducting layer of the planar optical waveguide 6. During passage through the planar optical waveguide 6, the propagation speed of the waveguide mode is influenced by reason of the evanescent field part, for instance by the chemical reactions taking place on the light-conducting layer. After having passed through the light-conducting layer of the optical waveguide 6, the light beams exit through an end face of the planar waveguide 6. The direction of propagation in the plane of the light-conducting film is here only changed by the refraction of the light. Light beams A, B are still divergent so that they become superimposed after a predetermined distance, and the diffraction pattern is obtained in a detection plane in which a CCD line 5 is arranged. In the plane perpendicular to the planar optical waveguide 6, the light can be collimated or a linear intensity distribution can be produced in the plane of detection by focusing with a cylindrical lens.

In an alternative embodiment, a difference in the refractive indices of two liquids or gases can be measured with the detector device (which is otherwise deactivated as described above) by replacing the planar optical waveguide 6 by a double cell or cuvette.

Figure 3:
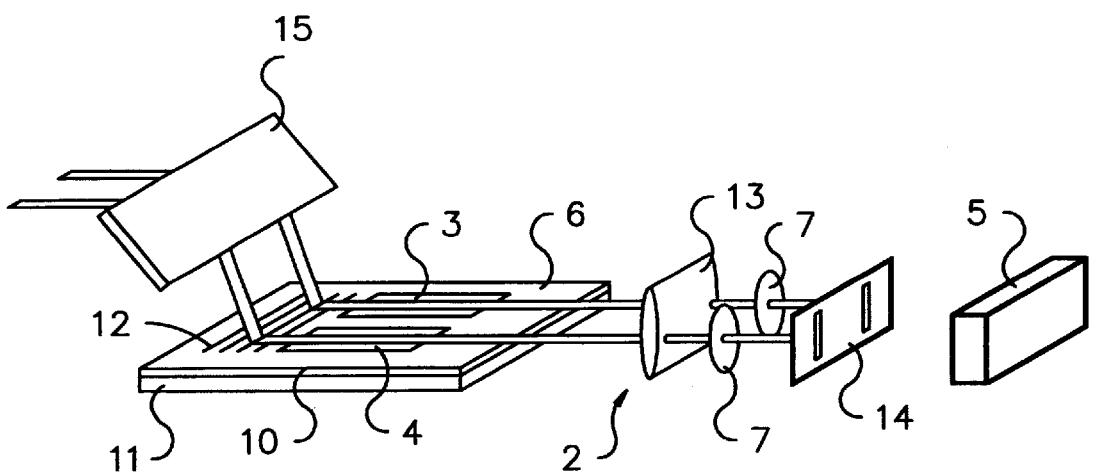
FIG. 3 is a schematic view showing an optical detector device according to a further embodiment of the invention with a measurement path and a reference path, respectively, arranged upstream of a beam forming means.

A further embodiment of an optical detector device is schematically shown in FIG. 3. In this embodiment the action path, i.e. the measurement path 3 and the reference path 4, is arranged upstream, i.e. in front of the optical beam-forming means 2. In this case, too, the measurement path 3 and the reference path 4, respectively, are formed in an integrated optical element (IO element), i.e. in a layer waveguide or a planar optical waveguide 6 whose surface carries the light-conducting layer 10 on a substrate 11. Diffraction gratings 12 are here used for coupling the light into and out of the optical waveguide 6. After having passed through the optical waveguide 6, which in this instance is laterally unstructured again, the light beams are collimated by a cylindrical lens 13. Two focal points are produced with two spherical lenses 7. A double pinhole diaphragm 14 is positioned in the focal plane of the spherical lenses 7. After having passed through the double pinhole diaphragm 14, the divergently extending light beams (here not shown) are superimposed, resulting in the same signature in the CCD line 5 as in the embodiment shown in FIG. 2. A deflection mirror 15 is here used for coupling the beams into the coupling grating.

Figure 4:
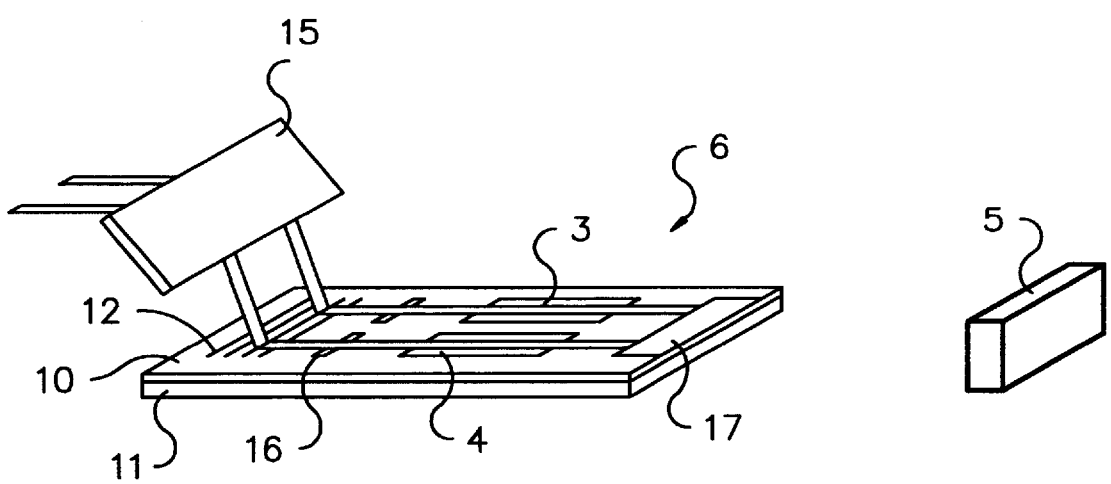
FIG. 4 shows an optical detector device according to a further embodiment of the invention with integration of the measurement path and reference path, respectively, and the beam forming means in an integrated optical component.

An embodiment of the integral configuration of the action region, i.e. of measurement path 3 and reference path 4, combined in one component with the optical beam-forming means in an integrated optical element, which is again designed as a layer waveguide (planar optical waveguide 6), is schematically shown in FIG. 4. Parallel light from a light source is coupled via a deflection mirror 15 through a coupling grating 12 into the planar optical waveguide 6. The planar waveguide 6 consists itself of a basic substrate 11 which is coated with the light-conducting layer 10. The light-conducting layer 10 of the optical waveguide 6 has formed therein planar lenses 16 which effect a light concentration in the plane of the light-conducting layer 10 of the optical waveguide 6. Said focusing lenses 16 are produced by increasing the effective refractive index of the waveguide mode. This can e.g. be effected by increasing the thickness of the light-conducting layer 10 in the area of the focusing lenses 16. Said planar lenses 16 focus the guided light passing through the measurement path 3 and reference path 4, respectively, onto planar slits to form a pair of radiation sources from which the light is radiated in divergent light beams from the end face of the optical waveguide 6 for superimposition in the detection plane of the CCD line 5. Such a slit can e.g. be produced in that in the area around the small exit opening of the light from the light-conducting layer 10 of the optical waveguide 6 the slit is given a highly light-absorbing characteristic, or in that the light is radiated in said area in another way.

An increase in the light absorbing capacity for forming the point-like radiation sources from which the light propagates as a divergent light beam can e.g. be achieved by metallic coatings 17 of the waveguide 6.

The other case, i.e. the formation of a point-like radiation source, can be realized by a defined interruption of the optical waveguide. For instance, the optical waveguide which is produced as a whole surface can be interrupted by structurized etching of its surface in the light-conducting layer thereof at places where the light is not to be passed on, but is to be radiated in a divergent manner.

Such a planar analogue to the formation of a double slit diaphragm would also work without the planar lenses. The focusing of the lenses onto the planar slit considerably increases the transmitted light intensity on the whole. When the lenses are used, the slit in such an embodiment (here not shown) filters undesired stray light out of the identity distribution subsequently received in the detection plane. It goes without saying that in this embodiment, too, the arrangement of the analyte and the reference liquid, respectively, e.g. by way of flow cells, in contact with the light-conducting layer (surface) of the planar optical waveguide 6 is only shown schematically and not in detail.

As the light-conducting layer element, it is also possible to use an integrated optical Y-distributor or divider as an element by which in a component the action path (reference path, measurement path) can be combined with the optical beam-forming means for forming the radiation sources which radiate the divergent beams. In contrast to the above-explained optical waveguides, the Y-distributor is here composed of strip lines. This means, that the Y-distributor has a lateral structurization with respect to its light-conducting layer so that specific optical paths are predetermined by said structurization of the optical waveguides. As for monomode waveguides, typical structural widths are in the order of a few micrometers. The Y-distributor divides the light coupled into an input over two outputs forming the radiation sources, Divergent beams which after a certain distance also produce a line pattern are created by diffracting the light exiting from the waveguide. The action by the substances or chemical reactions to be detected is again effected by the evanescent field of the strip line. A branch of said planar optical structure, which is designed as the Y-distributor, forms the measurement path while the other branch forms the reference path. The length of the action path can be defined very precisely by structurized cover layers. In such a case, too, preferably two different flow cells are mounted on the paths of the Y-distributor which carry the analyte (detection medium) on the one hand and reference liquids on the other hand.

Alternatively, it is also possible in this case to measure refractive indices of liquids or gases in that the surface of the Y-distributor remains unaffected but the Y-distributor has arranged thereafter a double cell or cuvette through which the light radiation exiting from the two paths of the radiation-sources of the Y-distributor passes divergently.

Both in this embodiment and in the previously explained embodiments, the refractive index of liquids can also be determined in that due to the evanescent field the phase velocity of the guided light wave also depends on a refractive index of the medium positioned above the light-conducting layer of the waveguide.

A line pattern, which is here only outlined schematically, is created in a detection plane. When coherent light is used, the intensity distribution can be described by a $\cos^2$ function, except for an intensity decline at the edge of the signature. When the phase velocity of light is changed in the area of measurement path and reference path, respectively, the signature will move laterally. The phase of said periodic distribution can be determined very exactly by various numerical methods.

Preferably, the signature received is evaluated with the help of a Fourier transform.

In the case of a lateral shift by one period of the signature or a multiple thereof, it is first difficult to obtain an unambiguous evaluation because in the case of a shift by exactly one period an identical identity distribution is obtained again. Such a difficulty can be avoided by using several, at least two, discrete optical wavelengths. Thus it is advantageous to operate with a light-different wavelength in measurement path and reference path at the same time. The resulting distribution is described by a $\cos^2$ function with a periodic envelope. The period of the envelope curve depends on the difference of the optical wavelengths used. The shift of the envelope curve corresponds to that of the original signature of a smaller period. The unambiguity range of the detection made can thereby be enlarged considerably.

Alternatively, and instead of coherent light, it is also possible to use light of a lower coherence in the measurement path and the reference path. In this case the $\cos^2$ function is superimposed by a non-periodic envelope and the position of a signature is determined by convolution with a function consisting of a periodic portion and a non-periodic envelope. An unambiguous evaluation will then be possible.

When light of lower coherence is used, the intensity distributions are preferably evaluated in the detection plane in two steps. First of all, a coarse search is conducted for determining the maximum of the envelope of the intensity distribution. This algorithm must at least be performed with an accuracy corresponding to the period of the diffraction pattern, so that the order of interference is clearly given. In a second step the phase position of the periodic intensity distribution is determined with a high resolution.

Preferably, said coarse search is carried out on the basis of a correlation between the signal received with the CCD line and two reference distributions. These reference distributions are numerically computed sine and cosine functions with a cosinoidal envelope. The modified cross-correlation yields a maximum at the position of the maximum of the envelope of the intensity distribution (interferometer signal). Starting from this position, a center of the intensity distribution is exactly determined by carrying out a Fourier transformation of the signal distribution.

Optionally, an FFT analysis (Fast Fourier Transformation) of the interferometer signal, i.e. the signature or intensity distribution, can be carried out. For an exact positional determination only those Fourier coefficients will be evaluated that are assigned to the local frequency at which the power spectrum has its maximum. Since the Fourier coefficients in the case of other local frequencies contain no information, it suffices to consider only said one local frequency.

As an alternative to the FFT algorithm, the Fourier coefficients are only calculated at the local frequency of the signal by using numerically computed sine and cosine functions. The phase is determined by calculating the arc tangent of the ratio of the Fourier coefficients.

Hence, within the scope of the implementation of such detector devices, coherent light, preferably also light of a smaller coherence length or light with several wavelengths, can be used at the same time.

Apart from the optical detector device as explained with reference to embodiments and outlined in more detail in the present claims, the above-explained measuring and evaluating method is also essential for the invention.

In the analytical field the parallel detection of many substances is an important objective of present and future developments. At the moment, so-called microtiter plates are normally used in automatic analyzers, the plates comprising 8×12 wells on their surfaces. The plates have a standard size of 8.6×12.8 cm. The development tends towards smaller analytical amounts (smaller amounts of detection medium) and a greater number of measurement points.

According to a further embodiment analyses can also be carried out in such a mictrotiter plate size, or in similar assemblies of many miniaturized containers for reagents, on the basis of the present detector device and the measuring method, respectively.

Figure 5:
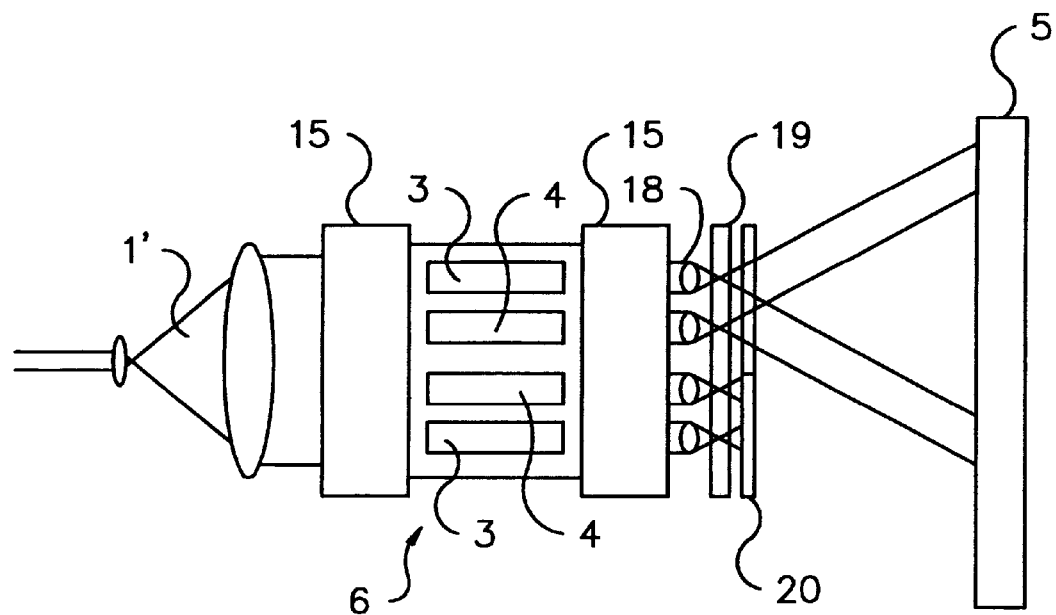
FIG. 5 is a schematic view showing an optical detector device according to a further embodiment of the invention with a multi-channel configuration.

Such an embodiment is shown in FIG. 5 which constitutes a further development towards multichannel analysis with respect to the embodiment of FIG. 3. Similar to the Young interferometer, a laser beam, here an expanded laser beam 1', is coupled via a deflection mirror 15 and a coupling grating (here not shown) into the integrated optical component, the planar optical waveguide 6, so that the optical waveguide 6 which is provided with the light-conducting layer on its surface is illuminated over its total width. A great number of measuring windows are defined on the surface of the optical waveguide 6 by way of photo-lithographic processing. In the present case there are provided four measuring windows, i.e. a respective pair consisting of a measurement path 3 and a reference path 4, which virtually represent two interferometers. After light has been coupled out and guided over a further deflection mirror 15, a focusing onto slit diaphragms 18 is carried out with a lens array 19 which can preferably be realized with micro-optical lens systems (e.g. spherical lenses) or with GRIN lenses. If only one CCD line 5 is used, the individual interferometers, each formed by a respective measurement path 3 and a reference path 4, must be read out alternately in time. To this end there is preferably provided an electronically controllable liquid crystal field 20 which passes the output of an interferometer onto the CCD line 5, but blocks the outputs of the other (in this instance, the second) interferometer. As a consequence, only the signature of one interferometer will appear on the CCD line 5 at a time. Since the immune reactions take place at a relatively slow pace during the analysis of biochemical reactions, the speed demands made on multiplexing are very low. In this case, too, the arrangement of the lens array that is focusing onto the slit diaphragms is optional, but advantageous in the interest of a signal intensity.

As an alternative to the embodiment shown in FIG. 5, a separate pair of coupling gratings for coupling light in and out may be provided at each measuring point, i.e. at each reference path and each measurement path. Reading out may be performed simultaneously for each row of wells in which the detection media and the reference media, respectively, are positioned. A next row of samples can be analyzed by mechanically displacing the carrier plate (in the form of microtiter plates) or by light guidance relative to the reference and measurement paths formed.

It is thereby possible to multiply an integrated optical Y-divider to obtain a multichannel detector in which several Y-dividers are used in a series arrangement in such a manner that the two radiation sources at the output of an Y-divider form the input light source for two subsequent Y-dividers.

Figure 6:
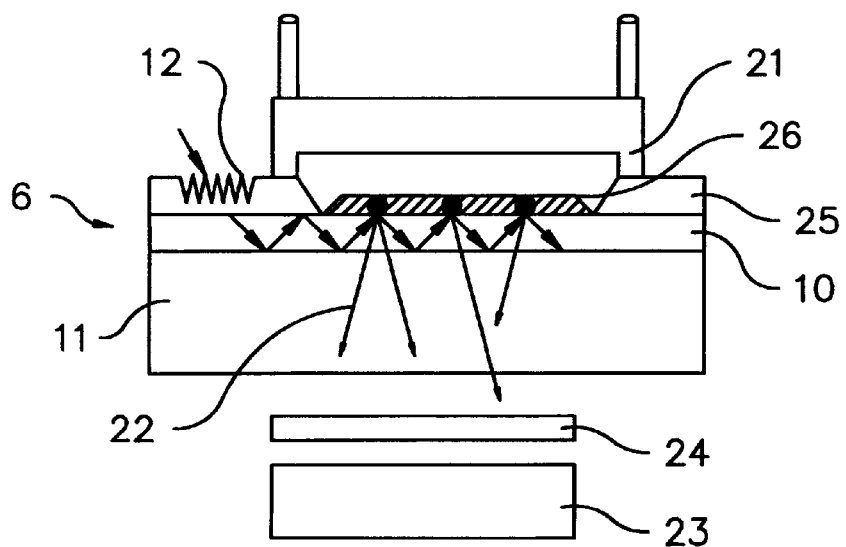
FIG. 6 is a schematic view showing an optical detector device (in part) in combination with fluorescence detection.

A further embodiment (of a channel, i.e. measurement or reference path) is shown in FIG. 6. The particular feature of said embodiment is that in this instance the optical detection of a medium guided through a cell or cuvette 21 and circulating, for instance, in the direction of the arrow through cell or cuvette 21 simultaneously senses a fluorescent radiation 22 of said medium and is preferably obtained by means of a photoamplifier 23, preferably with a filter 24 arranged upstream thereof, across the transparent or translucent substrate 11.

Hence, in such a case, additional information about the medium to be detected (in addition to the optical evaluation by superimposition of the convergent light beams of measurement path and reference path) can be obtained and compared by way of corresponding fluorescent radiation measurements, and a further criterion of distinction is thus available, for instance, for the analyte.

In this embodiment (which is only a schematic section through the measurement path in the planar optical waveguide 6), use is also made of a planar optical waveguide 6 which consists of (transparent or translucent) substrate 11 and light-conducting layer 10, and whose waveguide (light-conducting layer 10) is covered by a cover layer 25 leaving free a region in which the cell or cuvette 21 with the analyte 26 is brought into contact with the light-conducting layer 10.

Light is coupled in via a coupling grating 12 and reflected in the light-conducting layer so that after having passed through the light-conducting layer 10, e.g. as in the embodiment according to FIG. 3 or 4, it can be further processed.

At the same time, however, the light sets off a fluorescent radiation 22 in the analyte 26, the radiation being photoelectrically sensed across the substrate 11 at the bottom side of the optical waveguide 6.

Such a fluorescent characteristic may either be inherent to the analyte 26 or it may be imparted to the analyte by corresponding labeling with fluorescent material.

Optionally, other radiation emissions may be sensed as additional information, e.g. radioactive radiation after the analyte has been inoculated with corresponding substances. Preferably, however, light-dependent radiation characteristics of the analyte, in particular fluorescence, are used for gaining additional information. Such a fluorescent radiation may also be detected in another way, i.e. also at other places with respect to the optical waveguide 6.

The present invention provides an optical detector device which can be used for many analytical purposes and is of a robust and simple structure and which can be replaced rapidly so that the demands made in practice on the provision of a detection element for chemical or biochemical reactions on an optical basis are satisfied in a particularly advantageous manner.

What is claimed is:

1. An optical detector device for analyzing substances, mixtures of substances or chemical reactions and for determining refractive indices, comprising:
   a light source,
   a measurement path,
   a reference path, and
   optoelectronic detection means, said optoelectronic detection means comprising an optical divider arranged downstream of the light source for forming two radiation sources (9, 9') for divergently radiated light beams, one light beam having assigned thereto the measurement path (3) and one light beam having assigned thereto the reference path (4), the phase velocity of the light being influenced at least in the measurement path (3), and the divergent light beams being superimposed in the area of the optoelectronic detection means (5) to form a characteristic intensity distribution.

2. The optical detector device according to claim 1, wherein light emitted from the light source is guided at least in part in a planar waveguide (6).

3. The optical detector device according to claim 1, wherein the two radiation sources (9, 9') radiate coherent light or light of a small length of coherence.

4. The optical detector device according to claim 1, wherein light of different wavelengths is used at the same time.

5. The optical detector device according to claim 1, wherein an intensity distribution sensed with the optoelectronic detection means (5) can be evaluated with the help of a Fourier transform.

6. The optical detector device according to claim 5, wherein a position of an intensity of the intensity distribution is determined with a non-periodic envelope by convolution with a function consisting of a periodic portion and a non-periodic envelope.

7. The optical detector device according to claim 1, wherein the light beams freely pass through a detection medium and a reference medium, respectively.

8. The optical detector device according to claim 7, wherein the detection and reference media are positioned in flow cells or in test cells or cuvettes (21).

9. The optical detector device according to claim 1, wherein at least a detection medium (26) has fluorescent characteristics and fluorescent radiation (22) radiated by the detection medium upon irradiation with the light beam guided in the measurement path is supplied to a receiving means (23).

10. The optical detector device according to claim 9, wherein the receiving means contains a photodetector (23) with a filter (24) arranged upstream thereof.

11. The optical detector device according to claim 9, wherein the light beam assigned to the measurement path (3) is coupled into a planar optical waveguide (6) provided in part with a cover layer (25), and, in an exposed region of a light-conducting layer (10) of the optical waveguide (6), a cell or cuvette (21) with the detection medium (26) is in contact with said layer.

12. The optical detector device according to claim 11, wherein the fluorescent radiation (22) irradiated by the detection medium (26) can be detected, across a transparent substrate (11) of the optical waveguide (6), by the receiving means (23) which is arranged in the area of a back of the planar waveguide.

13. The optical detector device according to claim 1, wherein the optical divider is arranged upstream of the measurement and reference paths (3, 4).

14. The optical detector device according to claim 1, wherein the optical divider is arranged downstream of the measurement and reference paths (3, 4).

15. The optical detector device according to claim 1, wherein the optical divider and the measurement and reference paths (3, 4) are integrated into an optical element, in particular a planar optical waveguide (6).

16. The optical detector device according to claim 1, wherein the optical divider is an optical beam-forming means (2) with a focusing lens and a Köster's prism (8).

17. The optical detector device according to claim 16, wherein the Köster's prism (8) has arranged downstream thereof a planar optical waveguide (6) which divergently guides the two diverging light beams in a plane of a light-conducting layer (10) of the planar optical waveguide (6).

18. The optical detector device according to claim 17, wherein downstream of the optical waveguide (6) the light beams are collimated or focused with a cylindrical lens in a plane perpendicular to the optical waveguide (6) for producing a linear intensity distribution.

19. The optical detector device according to claim 1, wherein the measurement and reference paths (3, 4) are formed in a planar, laterally unstructurized optical waveguide (6), in which paths of parallel light beams can be coupled in and/or out via coupling gratings (12), and downstream of the optical waveguide a cylindrical lens assembly (13) is arranged followed by a pair of spherical lenses (7) in focal planes of which a double pinhole diaphragm (14) is arranged and the divergent light beams extending therefrom are received by a CCD line (5).

20. The optical detector device according to claim 1, wherein the measurement and reference paths (3, 4) are formed by a planar, laterally unstructurized optical waveguide (6), in which paths of parallel light beams can be coupled in via a coupling grating (12), and in a light-conducting layer (10) of the optical waveguide (6), downstream of the measurement and reference paths (3, 4), a pair of planar slits is arranged for forming divergent light beams which can be detected by a CCD cell (5).

21. The optical detector device according to claim 20, wherein upstream of the planar slits, planar lenses (16) are arranged for focusing guided light in a direction onto the planar slits for increasing an intensity of a signal gain.

22. The optical detector device according to claim 21, wherein the planar lenses (16) are formed by increasing an effective refractive index of the optical waveguide structure by an increased thickness of the light-conducting layer (10) of the optical waveguide (6).

23. The optical detector device according to claim 21, wherein the planar slits are realized by a metallic coating (17) of the planar optical waveguide (6).

24. The optical detector device according to claim 21, wherein the planar slits are realized by a defined interruption of the light-conducting layer of the planar optical waveguide by structurized etching of the surface of the optical waveguide which is coated over the whole surface with the light-conducting layer.

25. The optical detector device according to claim 1, wherein the measurement and reference paths (3, 4) are formed in an integrated optical Y-divider that forms a laterally structurized, planar optical waveguide.

26. The optical detector device according to claim 1, wherein the optical detector device has a multichannel arrangement.

27. The optical detector device according to claim 26, wherein a planar optical waveguide (6) comprises a plurality of measurement and reference paths, (3, 4) and, at the end or downstream of the optical waveguide (6), a plurality of radiation sources are formed which are assigned to the measurement and reference paths and radiate divergent light beams and which have assigned thereto a selection means (20) and have arranged downstream thereof the photoelectric detection means (5).

28. The optical detector device according to claim 27, wherein the radiation sources are formed by a controllable slit diaphragm assembly (19).

29. The optical detector device according to claim 28, wherein the measurement and reference paths (3, 4) of the optical waveguide (6) have assigned downstream of said waveguide a lens assembly (18) for focusing the light exiting from the optical waveguide (6) onto the slit diaphragm assembly (19).

30. The optical detector device according to claim 27, wherein the selection means is an electro-optically switchable liquid crystal field (20) for selecting a pair of action channels each formed of a measurement path (3) and an associated reference path (4).

31. The optical detector device according to claim 27, wherein a deflection mirror assembly (15) is provided upstream and downstream of the optical waveguide (6).

32. The optical detector device according to claim 27, wherein the plurality of measurement and reference paths (3, 4) of the optical waveguide are jointly acted upon by the light source after beam expansion.

* * * * *

UNITED STATES PATENT AND TRADEMARK OFFICE
CERTIFICATE OF CORRECTION

PATENT NO. : 6,239,876 B1
DATED : May 29, 2001
INVENTOR(S) : Albrecht Brandenburg It is certified that error appears in the above-identified patent and that said Letters Patent is hereby corrected as shown below:

<u>Title page,</u>
Item [75], Inventor, should read as follows -- Albrecht Brandenburg --
Item [73], Assignee, should read as follows -- Fraunhofer-Gesellschaft zur Förderung der Angewandten Forschung e. V., Munich (DE) --.

Signed and Sealed this

Thirteenth Day of August, 2002

*Attest:*

JAMES E. ROGAN
*Attesting Officer*  *Director of the United States Patent and Trademark Office*